(12) United States Patent
Adler (10) Patent No.: US 10,499,813 B2
(45) Date of Patent: Dec. 10, 2019

(54) METHODS, SYSTEMS AND APPARATUS FOR TEMPORAL CALIBRATION OF AN INTRAVASCULAR IMAGING SYSTEM

(71) Applicant: LightLab Imaging, Inc., Westford, MA (US)

(72) Inventor: Desmond Adler, Concord, MA (US)

(73) Assignee: LIGHTLAB IMAGING, INC., Westford, MA (US)

(*) Notice: Subject to any disclaimer, the term of this patent is extended or adjusted under 35 U.S.C. 154(b) by 1132 days.

(21) Appl. No.: 14/484,832

(22) Filed: Sep. 12, 2014

(65) Prior Publication Data
US 2016/0073885 A1    Mar. 17, 2016

(51) Int. Cl.
*A61B 5/00*    (2006.01)
*A61B 6/00*    (2006.01)
(Continued)

(52) U.S. Cl.
CPC .......... *A61B 5/0035* (2013.01); *A61B 5/0066* (2013.01); *A61B 5/0084* (2013.01); *A61B 5/02007* (2013.01); *A61B 6/504* (2013.01); *A61B 6/5205* (2013.01); *A61B 6/5247* (2013.01); *A61B 6/545* (2013.01); *A61B 6/58* (2013.01); *A61B 6/582* (2013.01); *A61B 6/488* (2013.01); *A61B 8/12* (2013.01); *A61B 2560/0223* (2013.01); *A61B 2560/0238* (2013.01); *A61B 2576/02* (2013.01)

(58) Field of Classification Search
CPC .... A61B 2560/0223; A61B 2560/0238; A61B 2576/02; A61B 5/0035; A61B 5/0066; A61B 5/0084; A61B 5/02007; A61B 6/504; A61B 6/5205; A61B 6/5247; A61B 6/582; A61B 8/12; A61B 6/58; A61B 6/545; A61B 6/488
See application file for complete search history.

(56) References Cited

U.S. PATENT DOCUMENTS 4,548,473 A    10/1985  Lo et al.
5,321,501 A    6/1994   Swanson et al.
(Continued)

FOREIGN PATENT DOCUMENTS

JP    63-127201    5/1988
JP    2010-148778  7/2010
(Continued)

OTHER PUBLICATIONS

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.
(Continued)

*Primary Examiner* — Amanda Lauritzen Moher
(74) *Attorney, Agent, or Firm* — K&L Gates LLP (57) ABSTRACT

In part, the disclosure relates to systems for imaging a blood vessel using intravascular image data and extravascular image data and methods to calibrate such systems. In one embodiment, multiple calibration trials are performed to determine a plurality of time lag values. A minimum time lag value is used to align intravascular image data and extravascular time lag data in one embodiment.

12 Claims, 6 Drawing Sheets

(51) Int. Cl.
*A61B 5/02* (2006.01)
*A61B 8/12* (2006.01)

(56) References Cited

U.S. PATENT DOCUMENTS

| | | | |
|---|---|---|---|
| 5,459,570 A | 10/1995 | Swanson et al. | |
| 5,465,147 A | 11/1995 | Swanson | |
| 5,509,093 A | 4/1996 | Miller et al. | |
| 5,518,810 A | 5/1996 | Nishihara et al. | |
| 5,586,201 A | 12/1996 | Whiting et al. | |
| 5,619,368 A | 4/1997 | Swanson | |
| 5,632,767 A | 5/1997 | Sinofsky | |
| 5,643,253 A | 7/1997 | Baxter et al. | |
| 5,715,827 A | 2/1998 | Corl et al. | |
| 5,748,598 A | 5/1998 | Swanson et al. | |
| 5,784,352 A | 7/1998 | Swanson et al. | |
| 5,822,391 A | 10/1998 | Whitting | |
| 5,908,415 A | 6/1999 | Sinofsky | |
| 5,947,959 A | 9/1999 | Sinofsky | |
| 5,965,355 A | 9/1999 | Swanson et al. | |
| 6,111,645 A | 8/2000 | Tearney et al. | |
| 6,134,003 A | 10/2000 | Tearney et al. | |
| 6,148,095 A | 11/2000 | Prause et al. | |
| 6,160,826 A | 12/2000 | Swanson et al. | |
| 6,191,862 B1 | 2/2001 | Swanson et al. | |
| 6,195,445 B1 | 2/2001 | Jolly et al. | |
| 6,270,492 B1 | 8/2001 | Sinofsky | |
| 6,282,011 B1 | 8/2001 | Tearney et al. | |
| 6,302,875 B1 | 10/2001 | Makower et al. | |
| 6,348,960 B1 | 2/2002 | Etori et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,565,514 B2 | 5/2003 | Svanerudh et al. | |
| 6,570,659 B2 | 5/2003 | Schmitt | |
| 6,692,824 B2 | 2/2004 | Benz et al. | |
| 6,706,004 B2 | 3/2004 | Tearney et al. | |
| 6,718,089 B2 | 4/2004 | James et al. | |
| 6,728,566 B1 | 4/2004 | Subramanyan et al. | |
| 6,731,973 B2 | 5/2004 | Voith | |
| 6,760,112 B2 | 7/2004 | Reed et al. | |
| 6,879,851 B2 | 4/2005 | McNamara et al. | |
| 6,891,984 B2 | 5/2005 | Petersen et al. | |
| 6,932,809 B2 | 8/2005 | Sinofsky | |
| 6,937,696 B1 | 8/2005 | Mostafavi | |
| 6,942,657 B2 | 9/2005 | Sinofsky et al. | |
| 6,973,202 B2 | 12/2005 | Mostafavi | |
| 6,974,557 B1 | 12/2005 | Webler et al. | |
| 7,068,831 B2 | 6/2006 | Florent et al. | |
| 7,134,994 B2 | 11/2006 | Alpert et al. | |
| 7,191,100 B2 | 3/2007 | Mostafavi | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,298,478 B2 | 11/2007 | Gilbert et al. | |
| 7,301,644 B2 | 11/2007 | Knighton et al. | |
| 7,321,677 B2 | 1/2008 | Evron et al. | |
| 7,355,699 B2 | 4/2008 | Gilbert et al. | |
| 7,408,648 B2 | 8/2008 | Kleen et al. | |
| 7,412,141 B2 | 8/2008 | Gowda et al. | |
| 7,414,779 B2 | 8/2008 | Huber et al. | |
| 7,415,049 B2 | 8/2008 | Flanders et al. | |
| RE40,608 E | 12/2008 | Glover et al. | |
| 7,492,522 B2 | 2/2009 | Gilbert et al. | |
| 7,576,861 B2 | 8/2009 | Gilbert et al. | |
| 7,593,559 B2 | 9/2009 | Toth et al. | |
| 7,625,366 B2 | 12/2009 | Atlas | |
| 7,697,972 B2 | 4/2010 | Verard et al. | |
| 7,711,413 B2 | 5/2010 | Feldman et al. | |
| 7,729,746 B2 | 6/2010 | Redel et al. | |
| 7,742,797 B2 | 6/2010 | Redel et al. | |
| 7,783,337 B2 | 8/2010 | Feldman et al. | |
| 7,792,342 B2 | 9/2010 | Barbu et al. | |
| 7,813,609 B2 | 10/2010 | Petersen et al. | |
| 7,848,791 B2 | 12/2010 | Schmitt et al. | |
| 7,853,316 B2 | 12/2010 | Milner et al. | |
| 7,869,663 B2 | 1/2011 | Buckland et al. | |
| 7,872,759 B2 | 1/2011 | Tearney et al. | |
| 7,916,387 B2 | 3/2011 | Schmitt et al. | |
| 7,918,793 B2 | 4/2011 | Altmann et al. | |
| 7,925,327 B2 | 4/2011 | Weese | |
| 7,930,014 B2 | 4/2011 | Huennekens et al. | |
| 7,935,060 B2 | 5/2011 | Schmitt et al. | |
| 7,967,743 B2 | 6/2011 | Ishihara | |
| 7,988,633 B2 | 8/2011 | Hossack et al. | |
| 7,991,105 B2 | 8/2011 | Mielekamp et al. | |
| 8,029,447 B2 | 10/2011 | Kanz et al. | |
| 8,116,605 B2 | 2/2012 | Petersen et al. | |
| 8,206,374 B2 | 6/2012 | Duane et al. | |
| 8,206,377 B2 | 6/2012 | Petroff | |
| 8,259,303 B2 | 9/2012 | Johnson et al. | |
| 8,290,228 B2 | 10/2012 | Cohen et al. | |
| 8,298,147 B2 | 10/2012 | Huennekens et al. | |
| 8,325,419 B2 | 12/2012 | Schmitt | |
| 8,351,665 B2 | 1/2013 | Tearney et al. | |
| 8,358,461 B2 | 1/2013 | Huber et al. | |
| 8,412,312 B2 | 4/2013 | Judell et al. | |
| 8,423,121 B2 | 4/2013 | Wang et al. | |
| 8,449,468 B2 | 5/2013 | Petersen et al. | |
| 8,457,375 B2 | 6/2013 | Rieber et al. | |
| 8,457,440 B1 | 6/2013 | Johnson | |
| 8,463,007 B2 | 6/2013 | Steinberg et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,542,900 B2 | 9/2013 | Tolkowsky et al. | |
| 8,556,820 B2 | 10/2013 | Alpert et al. | |
| 8,562,537 B2 | 10/2013 | Alpert et al. | |
| 8,571,639 B2 | 10/2013 | Mostafavi | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,670,603 B2 | 3/2014 | Tolkowsky et al. | |
| 8,687,201 B2 | 4/2014 | Adler | |
| 8,693,756 B2 | 4/2014 | Tolkowsky et al. | |
| 8,700,130 B2 | 4/2014 | Iddan et al. | |
| 8,781,193 B2 | 7/2014 | Steinberg et al. | |
| 8,786,336 B1 | 7/2014 | Schmitt | |
| 8,831,321 B1 | 9/2014 | Elbasiony | |
| 8,855,744 B2 | 10/2014 | Tolkowsky et al. | |
| 8,909,323 B2 | 12/2014 | Baumgart | |
| 8,913,084 B2 | 12/2014 | Chen et al. | |
| 8,948,228 B2 | 2/2015 | Adler | |
| 8,953,911 B1 | 2/2015 | Xu et al. | |
| 2002/0161351 A1 | 10/2002 | Samson et al. | |
| 2004/0006277 A1 | 1/2004 | Langenhove et al. | |
| 2005/0043614 A1 | 2/2005 | Huizenga et al. | |
| 2005/0201662 A1 | 9/2005 | Petersen et al. | |
| 2006/0095065 A1 | 5/2006 | Tanimura et al. | |
| 2006/0241465 A1* | 10/2006 | Huennekens | A61B 6/504 600/458 |
| 2006/0264743 A1 | 11/2006 | Kleen et al. | |
| 2007/0024617 A1 | 2/2007 | Poole | |
| 2007/0027390 A1 | 2/2007 | Maschke et al. | |
| 2007/0066890 A1 | 3/2007 | Maschke | |
| 2007/0135803 A1 | 6/2007 | Belson | |
| 2008/0194996 A1* | 8/2008 | Kassab | A61B 5/053 600/593 |
| 2008/0221439 A1 | 9/2008 | Iddan et al. | |
| 2008/0221440 A1 | 9/2008 | Iddan et al. | |
| 2008/0221442 A1 | 9/2008 | Tolkowsky et al. | |
| 2008/0283771 A1* | 11/2008 | Li | A61B 6/463 250/459.1 |
| 2009/0174931 A1 | 7/2009 | Huber et al. | |
| 2009/0306520 A1 | 12/2009 | Schmitt et al. | |
| 2010/0076320 A1 | 3/2010 | Petersen et al. | |
| 2010/0157041 A1 | 6/2010 | Klaiman et al. | |
| 2010/0160764 A1 | 6/2010 | Steinberg et al. | |
| 2010/0160773 A1 | 6/2010 | Cohen et al. | |
| 2010/0161022 A1 | 6/2010 | Tolkowsky et al. | |

(56) References Cited

U.S. PATENT DOCUMENTS

| | | | |
|---|---|---|---|
| 2010/0161023 A1 | 6/2010 | Cohen et al. | |
| 2010/0172556 A1 | 7/2010 | Cohen et al. | |
| 2010/0191102 A1 | 7/2010 | Steinberg et al. | |
| 2010/0222671 A1 | 9/2010 | Cohen et al. | |
| 2010/0228076 A1 | 9/2010 | Blank et al. | |
| 2010/0290693 A1 | 11/2010 | Cohen et al. | |
| 2011/0071404 A1 | 3/2011 | Schmitt et al. | |
| 2011/0101207 A1 | 5/2011 | Schmitt | |
| 2011/0157686 A1 | 6/2011 | Huber et al. | |
| 2011/0190586 A1 | 8/2011 | Kemp | |
| 2011/0228280 A1 | 9/2011 | Schmitt et al. | |
| 2011/0230758 A1 | 9/2011 | Eichler | |
| 2011/0319752 A1* | 12/2011 | Steinberg | A61B 6/12 600/424 |
| 2012/0004529 A1 | 1/2012 | Tolkowsky et al. | |
| 2012/0004537 A1 | 1/2012 | Tolkowsky et al. | |
| 2012/0029339 A1* | 2/2012 | Cohen | A61B 6/12 600/407 |
| 2012/0075638 A1 | 3/2012 | Rollins et al. | |
| 2012/0162660 A1 | 6/2012 | Kemp | |
| 2012/0310081 A1 | 6/2012 | Adler et al. | |
| 2012/0224751 A1 | 9/2012 | Kemp et al. | |
| 2012/0238869 A1 | 9/2012 | Schmitt et al. | |
| 2012/0250028 A1 | 10/2012 | Schmitt et al. | |
| 2012/0300215 A1 | 11/2012 | Johnson et al. | |
| 2012/0300216 A1 | 11/2012 | Johnson et al. | |
| 2013/0006105 A1 | 1/2013 | Furuichi | |
| 2013/0010303 A1 | 1/2013 | Petersen et al. | |
| 2013/0012811 A1 | 1/2013 | Schmitt et al. | |
| 2013/0023761 A1 | 1/2013 | Petroff | |
| 2013/0051728 A1 | 2/2013 | Petroff | |
| 2013/0072805 A1 | 3/2013 | Schmitt et al. | |
| 2013/0123616 A1 | 5/2013 | Merritt et al. | |
| 2013/0281832 A1 | 10/2013 | Baumgart et al. | |
| 2013/0310698 A1 | 11/2013 | Judell et al. | |
| 2014/0018669 A1 | 1/2014 | Xu | |
| 2014/0024931 A1 | 1/2014 | Winston et al. | |
| 2014/0094660 A1* | 4/2014 | Tolkowsky | A61B 5/064 600/300 |
| 2014/0094689 A1 | 4/2014 | Cohen et al. | |
| 2014/0094691 A1 | 4/2014 | Steinberg et al. | |
| 2014/0094692 A1 | 4/2014 | Tolkowsky et al. | |
| 2014/0094693 A1 | 4/2014 | Cohen et al. | |
| 2014/0094697 A1 | 4/2014 | Petroff et al. | |
| 2014/0100451 A1 | 4/2014 | Tolkowsky et al. | |
| 2014/0107479 A1 | 4/2014 | Klaiman et al. | |
| 2014/0114182 A1 | 4/2014 | Petersen et al. | |
| 2014/0114184 A1 | 4/2014 | Klaiman et al. | |
| 2014/0114185 A1 | 4/2014 | Tolkowsky et al. | |
| 2014/0142427 A1 | 5/2014 | Petroff | |
| 2014/0142432 A1 | 5/2014 | Hutchins et al. | |
| 2014/0142436 A1 | 5/2014 | Hutchins et al. | |
| 2014/0187920 A1 | 7/2014 | Millett et al. | |
| 2014/0187929 A1 | 7/2014 | Schmitt et al. | |
| 2014/0218210 A1 | 8/2014 | De Jong et al. | |
| 2014/0218742 A1 | 8/2014 | Adler | |
| 2014/0249407 A1 | 9/2014 | Adler et al. | |
| 2014/0268167 A1 | 9/2014 | Friedman et al. | |
| 2014/0270445 A1 | 9/2014 | Kemp | |
| 2014/0276011 A1 | 9/2014 | Schmitt et al. | |
| 2014/0309536 A1 | 10/2014 | Douk et al. | |
| 2014/0379269 A1 | 12/2014 | Schmitt | |
| 2015/0141808 A1* | 5/2015 | Elhawary | A61B 5/0026 600/424 |

FOREIGN PATENT DOCUMENTS

| | | |
|---|---|---|
| JP | 2012-130680 | 7/2012 |
| JP | 2013-537444 | 4/2013 |
| WO | 2012176191 | 12/2012 |
| WO | 2013175472 | 11/2013 |
| WO | 2014002095 | 1/2014 |

OTHER PUBLICATIONS

International Search Report and Written Opinion mailed from the International Searching Authority dated Jun. 27, 2014 for International Application No. PCT/US2013/030623 (17 pages).

Dave Fornell, "The Advantages and Disadvantages of OCT vs. IVUS", Diagnostic and Interventional Cardiology, May 18, 2011, pp. 1-4.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Perez-Rovira et al., "Deformable Registration of Retinal Fluorescein Angiogram Sequences Using Vasculature Structures", 32nd Annual Conf. of IEEE EMBS, 2010, pp. 4383-4386.

International Search Report and Written Opinion of the International Searching Authority for International Application No. PCT/US2015/042849 mailed from the International Searching Authority dated Nov. 2, 2015 (16 pages).

International Preliminary Report on Patentability for International application No. PCT/US2015/042849 issued from the International Bureau of WIPO dated Mar. 14, 2017 (11 pages).

Written Opinion of the International Searching Authority for International Application No. PCT/US2008/012701, dated May 14, 2009 (10 pages).

International Search Report for International Application No. PCT/US2008/012701, dated May 14, 2009 (7 pages).

PCT International Preliminary Report on Patentability for International Application No. PCT/US2008/012701, dated May 18, 2010 (10 pages).

Annex to Form PCT/ISA206 Communication Relating to the Results of the Partial International Search for International Application No. PCT/US2008/012701, dated Feb. 27, 2009 (3 pages).

PCT International Search Report and Written Opinion of International Searching Authority for International Application No. PCT/US2013/078500, dated Jul. 8, 2014 (14 pages).

Tung et al., "Automatic Detection of Coronary Stent Struts in Intravascular OCT Imaging", Proceedings of SPIE, vol. 8315, Feb. 22, 2012 (8 pages).

JP 2017-534518, Notification of Reason(s) for Refusal, dated May 14, 2019, (5 pages).

* cited by examiner

METHODS, SYSTEMS AND APPARATUS FOR TEMPORAL CALIBRATION OF AN INTRAVASCULAR IMAGING SYSTEM

FIELD

In part, the disclosure relates generally to the field of vascular system and peripheral vascular system imaging and data collection.

BACKGROUND

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) and acoustic technologies such as intravascular ultrasound (IVUS) and others are also valuable tools that can be used in lieu of or in combination with fluoroscopy to obtain high-resolution data regarding the condition of the blood vessels for a given subject.

Intravascular optical coherence tomography is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a clinician to diagnose as well as monitor the progression of coronary artery disease. Angiography is a noninvasive x-ray imaging method that collects data from outside the body during injection of a radio-opaque contrast fluid.

Given the complexity of the various technologies described above and the associated complexity of the datasets each of them generate, co-registering such datasets is difficult. If the relevant systems, such as for example an angiography system and an OCT system, are not calibrated to one another, the likelihood of achieving accurate co-registration is low.

Accordingly, a need therefore exists to provide suitable calibration methods and systems suitable for increasing coregistration accuracy. Embodiments of the disclosure address these challenges and others.

SUMMARY

In part, the disclosure relates to a multimodal diagnostic system and components thereof configured to co-register two or more of the following OCT, IVUS, FFR, and angiography. In one embodiment, OCT images and angiography images are co-registered after calibrating a combined OCT and x-ray imaging system to determine a time delay to align or synchronize the two sets of frames of image data. In one embodiment, the time delay is determined based upon a minimum value from multiple calibration trials. As discussed herein, angiography systems can be used to obtain a cine sequence or set of cine images. Such a set or sequence includes one or more images that are obtained over time. This set of images is effectively a short movie with each image being a frame that can track and show movement and cardiovascular system changes as the heart progresses through the cardiac cycle.

The initiation of an x-ray based imaging system such an angiography system can be caused by one or more control signals sent from one or more control systems. Similarly, the initiation of an intravascular imaging system such an OCT system can be caused by one or more control signals sent from one or more control systems to a patient interface unit or PIU. During an OCT data collection session, the optical fiber and associated lens positioned to send and receive light rotates within a blood vessel. The PIU to which an intravascular data collection probe connects receives a control signal which causes the probe tip to rotate and then translates the probe tip as part of a pullback through the blood vessel.

Initially, the probe tip captures an image along a ray or scan line as it rotates prior to translation along a support. In one embodiment, an angiography initiating control signal is transmitted prior to transmitting an OCT initiating control signal. As a result, the angiography system captures one or more frames of angiography images such as J frames of angiography data prior to capturing a first frame of OCT image data. The first frame of OCT image data can include images obtained while the probe tip rotates prior to being translated along a vessel during a pullback.

In part, the disclosure relates to a method of calibrating a combination angiography and an optical coherence tomography (OCT) system. The method can include acquiring angiography frames prior to initiation of an OCT probe pullback; acquiring OCT data during the OCT probe pullback; acquiring angiography frames during the OCT probe pullback; generating a plurality of OCT frames using the OCT data obtained during the pullback; determining an initial frame of the OCT probe pullback from the plurality of OCT frames; determining an initial angiography frame that corresponds to the initial frame of OCT probe pullback; determining a time delay between the initial OCT frame and the initial angiography frame; and aligning OCT and angiography frames using the time delay.

In one embodiment, the method further includes displaying one or more aligned OCT frames and angiography frames. In one embodiment, determining a time delay includes performing a plurality of calibration trials to determine a plurality of delay periods and selecting the minimum delay period as the time delay. In one embodiment, the plurality of calibration trials is N trials, wherein N ranges from 2 trials to about 12 trials. In one embodiment, the method further includes initiating the OCT pullback at an initiation time, wherein a computing device stores the initiation time in memory. In one embodiment, determining the initial frame of the OCT probe pullback includes identifying the OCT frame corresponding to the initiation time as the initial frame of the OCT probe pullback. In one embodiment, determining the initial angiography frame includes determining a first angiography frame indicative of movement of a marker attached to the OCT probe and selecting a second angiography frame preceding the first angiography frame as the initial angiography frame.

In part, in one embodiment, the disclosure relates to a method of calibrating an optical coherence tomography system and an angiography system. The method includes generating N sets of optical coherence tomography (OCT) image data, wherein each of the N sets of OCT image data is obtained by performing N ex vivo pullbacks of an intravascular data collection probe comprising a marker; generating N sets of angiography image data comprising a plurality of two-dimensional images, wherein each of the N sets of angiography image comprise a plurality of two-dimensional images of the marker in two or more different spatial positions; generating N sets of OCT frames using the N sets of OCT image data obtained during the N ex vivo pullbacks; determining an initial frame of the OCT probe pullback from the plurality of OCT frames for each set N; determining an initial angiography frame that corresponds to the initial frame of OCT probe pullback for each set N; determining a time delay between the initial OCT frame and the initial angiography frame for each set N such that N time delays are determined; selecting a minimum time delay from the N time delays; and aligning OCT and angiography frames using the minimum time delay.

In one embodiment of the method, determining the initial angiography frame includes determining a first angiography frame indicative of movement of a marker attached to the OCT probe and selecting a second angiography frame preceding the first angiography frame as the initial angiography frame. In one embodiment, N ranges from 2 to 12. In one embodiment, the method further includes initiating the OCT pullback at an initiation time, wherein a computing device stores the initiation time in memory. In one embodiment of the method, determining the initial frame of the OCT probe pullback includes identifying the OCT frame corresponding to the initiation time as the initial frame of an ex vivo pullback. In one embodiment, determining the initial angiography frame includes using a computing device to track pixel changes in angiography frames to identify marker movement. In one embodiment, a frame rate of the OCT system is greater than the frame rate of the angiography system.

In part, in one embodiment, the disclosure relates to a system for calibrating a combination intravascular and extravascular imaging system. The calibration system can include an x-ray based imaging subsystem and an optical imaging subsystem such as an interferometry-based subsystem. In one embodiment, the calibration system includes an optical coherence tomography (OCT) probe comprising a marker, wherein the probe is disposed on a support and disposed within an imaging zone of an angiography system; an optical coherence data processing system comprising a computing device, wherein the computing device generates frames of OCT images based upon received intravascular probe signals; one or more memory devices; and a control signal input in electrical communication with the one or more memory devices, wherein the control signal input is in electrical communication with a controller programmed to initiate a plurality of ex vivo pullbacks of the OCT probe and transmit each ex vivo pullback initiation time to the one or more memory devices.

The computing device can include, in an embodiment, a calibration method stored in the one or more memory device as instructions to cause the computing device to determine an initial frame of the OCT probe for each ex vivo pullback. The computing device can include, in an embodiment, a calibration method stored in the one or more memory device as instructions to cause the computing device to determine an initial angiography frame that corresponds to the initial frame of OCT probe pullback. The computing device can include, in an embodiment, a calibration method stored in the one or more memory device as instructions to cause the computing device to determine a time delay between the initial OCT frame and the initial angiography frame. The computing device can include, in an embodiment, a calibration method stored in the one or more memory device as instructions to cause the computing device to align OCT and angiography frames using the time delay.

In part, the disclosure relates to a method of imaging a blood vessel and/or calibrating a system that images a blood vessel. The method includes generating a set of intravascular image data comprising a plurality of intravascular image frames at a first frame rate using an intravascular imaging system comprising a first clock; storing the intravascular image data in one or more non-transitory computer readable memory devices; generating a set of extravascular image data comprising a plurality of extravascular image frames at a second frame rate using an extravascular imaging system comprising a second clock; storing the extravascular image data in one or more non-transitory computer readable memory devices. The method includes detecting motion in one of the plurality of frames. The frame preceding the frame having detected motion is selected as an initial frame in one embodiment. In one embodiment, the plurality of extravascular image frames comprises an angiography cine.

In one embodiment, an intravascular data collection system collects data simultaneously with but asynchronously relative to an extravascular data collection system. The method determines a delay or calibration period to synchronize frames obtained from the two asynchronous data collection systems. The method can include co-registering the OCT image data and the angiography data by aligning one or more OCT frames with one or more angiography frames by a calibration time period.

In one embodiment, the disclosure relates to a calibration method. The method includes synchronizing x-ray image frames and intravascular image frames using a calibration period determined from a plurality of trials. The method include programmatically generating a calibration period using an initial x-ray image frame having detected marker motion and an initial intravascular image frame determined by storing when a control signal to initiate marker motion is sent to an interface unit in mechanical communication with a marker and able to translate the marker over a plurality of positions.

In part, the disclosure relates to a method of calibrating a combination angiography and an optical coherence tomography (OCT) system. The method includes storing a plurality of angiography frames in one or more memory devices in electrical communication with a computing device; storing a plurality of OCT frames in one or more memory devices in electrical communication with the computing device, the OCT frames and angiography frames generated asynchronously during an overlapping time period corresponding to an OCT probe pullback; determining an initial frame of the OCT probe pullback from the plurality of OCT frames; determining an initial angiography frame that corresponds to the initial frame of OCT probe pullback; programmatically generating, using the computing device, a calibration period based upon a timestamp of the initial frame of OCT probe pullback and based upon a timestamp of the initial angiography frame; and synchronizing a plurality of the asynchronously generated OCT frames and angiography frames. In one embodiment, the computing device is a microprocessor or one or more circuits of an OCT data processing system. In one embodiment, the computing device is a microprocessor or one or more circuits of an angiography data processing system.

BRIEF DESCRIPTION OF THE DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

The following description refers to the accompanying drawings that illustrate certain embodiments of the present disclosure. Other embodiments are possible and modifications may be made to the embodiments without departing from the spirit and scope of the disclosure. Therefore, the following detailed description is not meant to limit the present disclosure; rather, the scope of the present disclosure is defined by the claims.

Intravascular data collection such as imaging of a blood vessel can be performed by inserting a catheter comprising a data collection probe into an artery and advancing it until it reaches a region of interest within a blood vessel, such a coronary artery. An angiography system can obtain external angiographic images of that vessel, such as a cine sequence, during the imaging of the blood vessel. In one embodiment, the region of interest is imaged by pulling the data collection probe through the catheter while optical, acoustic, or other sensors in the probe collect intravascular data. The process of pulling the data collecting probe through a region of interest in a blood vessel is referred to as a pullback in one embodiment. According to the disclosure, it is advantageous to initiate the angiography image capture prior to initiating the pullback for purposes of subsequently co-registering the angiographic and intravascular image data sets.

Co-registration of two or more imaging technologies such as angiography and OCT, for example, is challenging to implement. As disclosed herein, OCT/angiography or x-ray based coregistration ("angiography coregistration") methods facilitate visualization of a position of or a subset of an OCT image on a corresponding angiography image acquired at a similar point in time. Such coregistration methods can be implemented using hardware, software, or combinations thereof In part, the disclosure relates to various systems, components thereof, and methods for use in a catheter lab or other facility to perform one or more calibration processes to improve co-registration accuracy with respect to data collected with regard to a subject. In one embodiment, the data can include one or more cine sequences obtained using an x-ray system such as an angiography system. Further, the data can include intravascular data. An example of intravascular data is OCT data which can be obtained using an intravascular imaging probe and an OCT system. The OCT data can be stored in computer-readable memory as scan lines, images, or in other data formats. Intravascular ultrasound data is another type of intravascular data.

Figure 1:
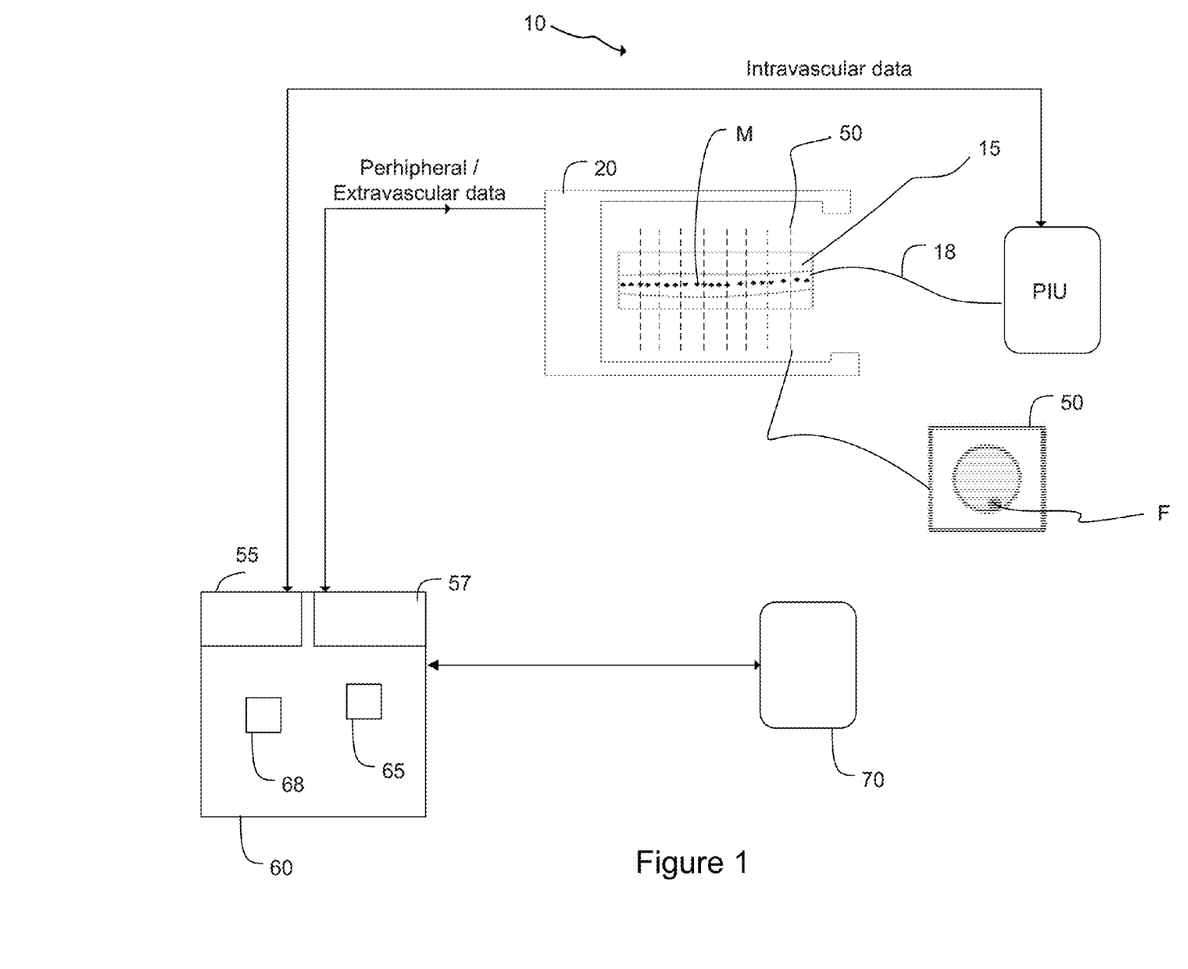
FIG. 1 is a schematic diagram of a data collection system that collects intravascular data and extravascular data during overlapping periods of time suitable for calibration using one or more methods of the disclosure.

FIG. 1 shows a system 10 that includes various data collection subsystems suitable for collecting data, detecting a feature of, sensing a condition, and imaging a region of interest in a subject using one or more imaging modalities or otherwise generating diagnostic data. The region of interest in a subject can include a blood vessel 15. In one embodiment, an intravascular data collection probe is pulled back through the vessel 15.

Examples of such probes include OCT, IVUS, FFR, or other data collection probes. The probe includes one or more of a guidewire, a pressure sensing wire-based probe, an optical fiber and other components. An optical fiber 18 is shown extending from where the probe would be disposed in the vessel 15. The tip of a given data collection probe can include a marker. These markers are identified by M as shown herein in the non-invasively acquired image frames such as the x-ray generated images. As shown in FIG. 1, a series of overlapping sequential angiography images are shown from a top down perspective with the dots corresponding to markers M shown over the sequence of their movement through the vessel 15. In one embodiment, the marker M is a radiopaque marker that is part of the data collection probe. For example, in one embodiment, a radiopaque marker M can be disposed near a lens or other beam-directing element of a probe. The points F in the OCT frames are included to illustrate a feature F that changes its appearance as the pullback progresses. In this way, different cross-sections of the blood vessel being imaged with different features F correspond to different positions in the angiography frames.

For a probe that includes an optical beam director or lens, the optical fiber is in optical communication with the beam director or lens. A torque wire can be part of the probe defines a bore in which an optical fiber is disposed. In addition, the probe also includes the sheath such as a polymer sheath (not shown) which forms part of a catheter. The optical fiber, which in the context of an OCT system is a portion of the sample arm of an interferometer, is optically coupled to a patient interface unit (PIU) as shown. The PIU can be operated using various controls that can be used to initiate the pullback of the probe through the vessel.

The data collection system 10 includes a noninvasive imaging system 20 such as a nuclear magnetic resonance, x-ray, angiography, computer aided tomography, or other suitable noninvasive imaging technology. As shown as a non-limiting example of such a noninvasive imaging system, an angiography system such as suitable for generating cines is shown. The angiography system can include a fluoroscopy system. The noninvasive imaging system collects extravascular or peripheral imaging data while the intravascular imaging probe pulled back through the vessel generates cross-sectional views 50 as shown. Theses intravascular images 50 can be cross-sectional view, longitudinal views, or other views generated using data from an intravascular data collection probe.

The noninvasive imaging system 20 and the PIU are in communication with separate data storage and processing systems 55, 57 or can be in communication with one data storage and processing system 60. One or more of such systems 55, 57, or 60 can be used individually or integrated together. These systems can be implemented as a workstation or server in one embodiment or generally as a computing device. A computing device may include a server computer, a client user computer, a personal computer (PC), a laptop computer, a tablet PC, a desktop computer, a control system, a microprocessor or any computing device capable of executing a set of instructions (sequential or otherwise) that specify actions to be taken by that computing device. Further, while a single computing device is illustrated, the term "computing device" shall also be taken to include any collection of computing devices that individually or jointly execute a set (or multiple sets) of instructions to perform any one or more of the software features or methods such as interface.

In one embodiment, the computing device is an optical coherence tomography computer programmed to perform one or more temporal calibration methods as described herein. The programs, instructions, and control signal information and related co-registration methods that can use a calibration time can be implemented using software instructions stored in memory 65 or as a hardware-based integrated circuit 68. In one embodiment, an external database 70 is used to store image frames, calibration time periods, co-registered OCT and x-ray images and other information described herein with respect to the systems and collected image data. The time delay outputs of multiple calibration trials can be stored in memory such as database 70 or in the systems described herein and ranked to select a minimum time delay using one or more processors or computing devices. In one embodiment, memory 65 receives an OCT pullback initiation time corresponding to one the OCT probe pullback starts. This initiation time can be correlated with a corresponding captured OCT frame, which can be identified as the initial frame of the OCT pullback.

The patient interface unit includes a probe connector suitable to receive an end of the probe and be optically coupled thereto. The PIU includes suitable joints and elements based on the type of data collection probe being used. In addition to being pulled back, the probe tip is also typically rotated by the PIU. In this way, a blood vessel of the subject 10 can be imaged longitudinally or via cross-sections.

In turn, the PIU is connected to one or more intravascular data collection systems 55 or 60 as described herein. The intravascular data collection system 55, 60 can be an OCT system, an IVUS system, another imaging system, and combinations of the foregoing. For example, the system 60 in the context of a probe being an OCT probe can include the sample arm of an interferometer, the reference arm of an interferometer, photodiodes, a control system, and patient interface unit.

The intravascular image data such as the frames of intravascular data generated using the data collection probe can be routed to the data collection processing system 60 coupled to the probe via PIU. The noninvasive image data generated using system 20 can be transmitted to, stored in, and processed by one or more computing devices. A video frame grabber device such as a computer board configured to capture the angiography image data from system 20 can be used in various embodiments as part of systems 55, 57, or 60.

Calibration and Co-registration

In one embodiment of a coregistration method, a set of angiography data such a cine sequence of images is acquired during an OCT pullback. Thus, as an OCT imaging probe is pulled back through a blood vessel as it rotates, the marker M disposed on or in the OCT probe moves with it and is identifiable and trackable in the set of simultaneously captured angiography frames. If a coregistration calibration method of the angiography system and the OCT system is not performed or is inadequate to calibrate the relevant imaging system, the OCT frames and the angiography frames may not be aligned.

In turn, this results in a failure to coregister the x-ray and optical imaging datasets. In addition, the failure to align the OCT and angiography datasets could result in errors such as positional cursor errors. Thus, the cursor used by a clinician or other system operators used to show where the OCT image was taken on the angiography image may be out of sync by several frames. This can cause a lack confidence in system users such that they doubt that the on screen cursor is actually showing them what it purports to show them. Additional details relating to the problems of a time lag and misalignment of OCT image frames and angiography image frames is described in more detail with regards to FIG. 2 and calibration system 100.

In one embodiment, two steps are performed to achieve accurate coregistration in conjunction with a calibrated multimodal imaging system such as an OCT and angiography system. The first step is identifying or locating a reference point or section of an intravascular data collection probe throughout a set of image frames such as angiography frames that constitute a cine sequence. The reference point or section can include a marker, a probe tip, a lens, a pressure transducer, a beam director, or other probe locus, portion, component or combinations thereof. All of the foregoing can be used as markers M shown in the relevant figures.

Thus, for an OCT imaging probe, a lens is used to direct and receive light and collect data that corresponds to depth measurements such that a tomographic image of the imaged region can be generated. The second factor is temporally aligning the angiographic and OCT data sets. In part, the disclosure relates to calibration methods that can be performed when installing an OCT system in catheter lab to operate in conjunction with an angiography system. The calibration of an OCT system is also performed when an angiography system is changed that is used in conjunction with the OCT system. When a change in such a multimodal imaging system occurs, re-calibration is often necessary to prevent or fix co-registration anomalies.

The calibration methods described herein improve the accuracy when co-registering a set of intravascular data, such as for example, a set of OCT images, and a set of peripheral or extravascular data such as a set of angiography images. In part, the disclosure relates to determining the relative time period between OCT and angiographic data sets. This time period can be determined and the can be used as a temporal calibration factor for the angiography coregistration software.

Figure 2:
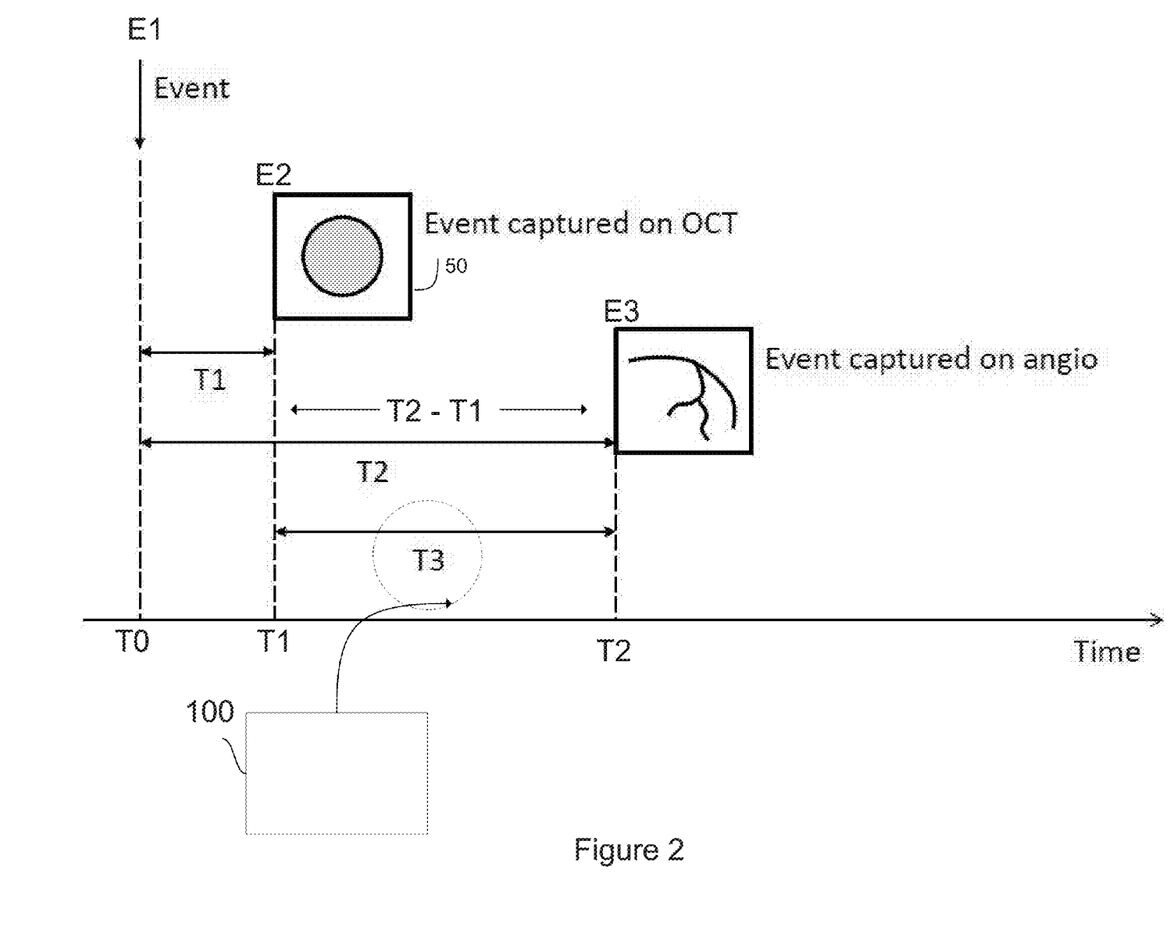
FIG. 2 is a schematic diagram of various data collection events and time periods that can be calibrated using one or more of the systems and methods described herein.

As shown in FIG. 2, in an angiography coregistration system, OCT and angiography image data are acquired simultaneously during an OCT catheter pullback with regard to blood vessel A physical event E1 in the real world (such as the initiation of the OCT catheter pullback) occurs at a certain point in time, indicated by the "Event" arrow such as a zero point in time, T0 or some other origin or reference point. This physical event E1 is subsequently captured in an OCT image frame, which can be considered as a second event E2 that is stored into computer memory at a future point in time "T1" after the physical event. Thus, the event capturing of the pullback initiation using OCT is event E2 which corresponds to the imaging of the blood vessel 15. The angiography system lags the OCT system such that the angiography image capture of the blood vessel 15 and the moving OCT probe disposed therein is delayed by a delay period T3 relative to the OCT image capture.

Similarly, the same physical event E1 is also captured in an angiography image frame that is stored into computer memory at a future point in time "T2" after the physical event E1 and after its OCT capture E2 as effectively a third event E3. The time periods T1 and T2 represent the finite time required to generate, transmit, and process the OCT and angiography images, respectively. In one embodiment, the time period T1 ranges from about several microseconds to about several seconds. In one embodiment, the time period T2 ranges from about several microseconds to about several seconds. In one embodiment, the time period T3 ranges from about several microseconds to about several seconds. The frame rate of an OCT system ranges from about 20 frames per second to about 1000 frames per second. The frame rate of a non-invasive imaging system such as an x-ray-based system ranges from about 10 frames per second to about 60 frames per second.

Since T1 and T2 may be different, a fixed time period T3 exists between when the OCT frame is stored into computer memory E2 and when the corresponding angiography frame is stored into computer memory E3. If this time period T3 is not compensated for, OCT frame positions are displayed on the incorrect angiography frame. In turn, such a failure to compensate for such a time lag T3 can lead to inaccuracies in coregistration. As described herein, T3 can be accurately determined using a calibration method.

In turn, with a T3 value determined using the systems and methods described herein, the OCT and angiography data sets can be temporally aligned. After alignment using the determined T3 value the OCT frame positions can be displayed on the correct angiography frame using the systems described herein. One or more calibration systems 100 can be used to determine T3. The calibration system can be implemented using one or more of the components of system 10 of FIG. 1, system 110 of FIG. 5A and system 120 of FIG. 6.

Figure 3:
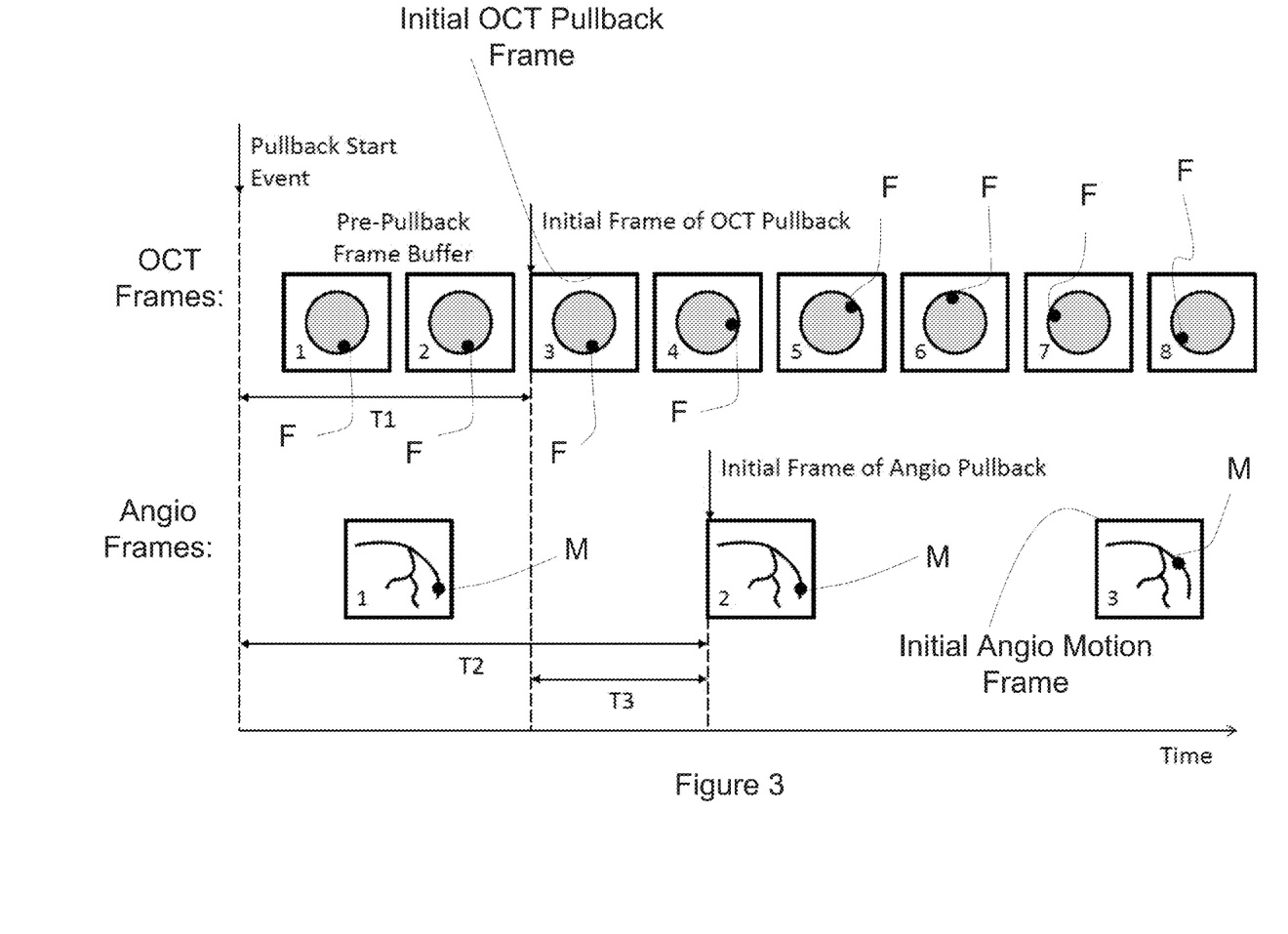
FIG. 3 is a schematic diagram illustrating various steps and events that can be implemented and tracked in conjunction with calibrating a multimodal imaging system and determining a calibration time period T3 according to an embodiment of the disclosure.

FIG. 3 illustrates a schematic representation of various image frames and method steps for determining the time period T3. First, an OCT pullback is acquired with simultaneous angiography. The frames shown at the top portion of FIG. 3 are frames of intravascular image data such as OCT data frames. An OCT image feature F is visible at a position within each OCT data frame and changes position when the OCT pullback commences. The frames below that include a top down view of an exemplary blood vessel are extravascular image data such as angiography data frames. Both datasets are generated, transmitted, processed, and stored in a central computer. The OCT dataset includes frames of OCT image data numbered from 1 to 8. In contrast, three frames of angiography image data numbered 1 to 3 are also shown. The OCT dataset includes a series of time stamped frames in the computer memory, where each timestamp represents the time at which the frame entered computer memory. The corresponding series of time stamped angiography frames is also present in computer memory. The timestamps are generated by a common system clock but are applied to each dataset independently. In one embodiment, the common system clock is the clock of the data processing system 60. The computer memory can be part of system 60 for example of FIG. 1 and similar data processing systems as described herein.

Next, a determination is made as to which OCT frame represents the initial frame of the pullback. A human may inspect the OCT image data and estimate which frame represents the initial frame of the pullback. Alternatively, a computing device can be used to determine the initial frame of the pullback such as by automatically logging the time at which a command was sent to initiate the OCT pullback. Machine vision and image processing software can also be used by a computing device to determine the initial frame of the pullback. In the example shown in FIG. 3, the initial OCT frame is the third frame of the dataset.

Figure 4:
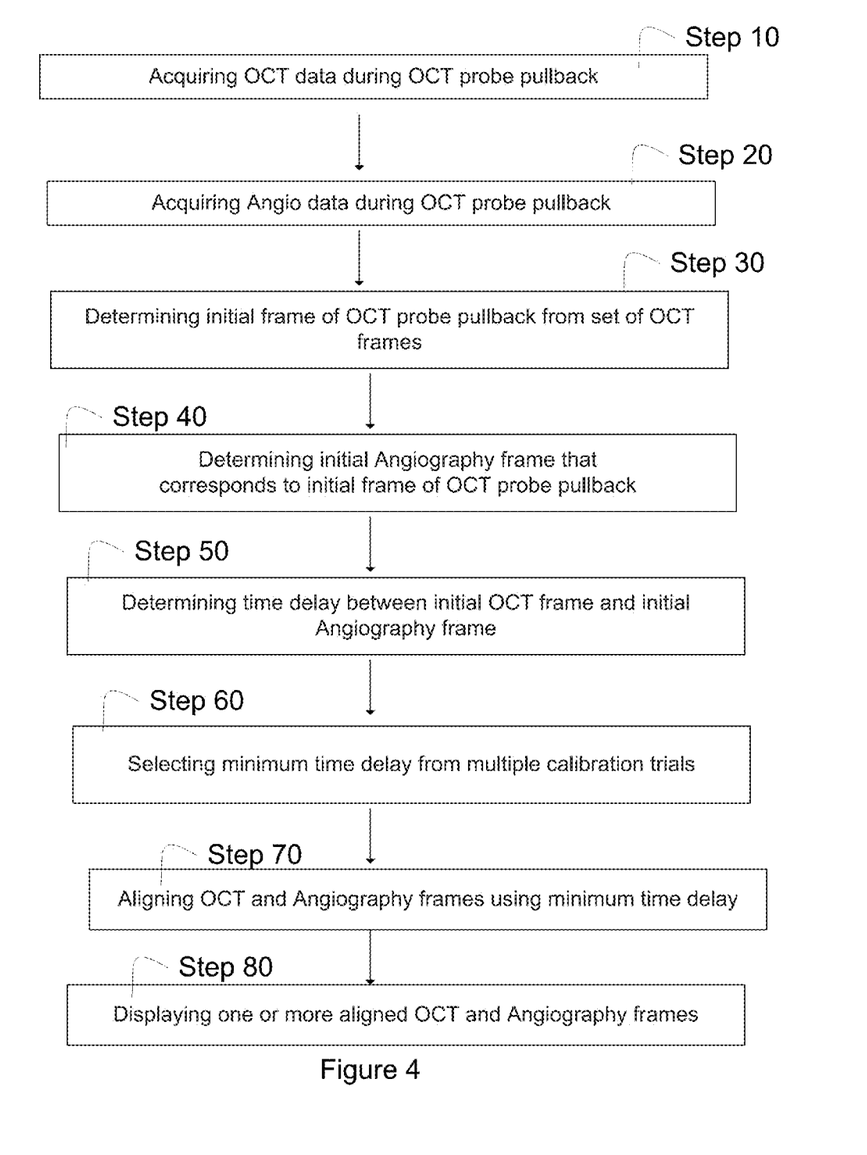
FIG. 4 is a schematic diagram illustrating various steps of an exemplary temporal calibration method suitable for increasing co-registration accuracy in a multimodal imaging system according to an embodiment of the disclosure.

Next, a determination is made as to which angiography frame represents the closest point in time to the initial OCT frame. This determination may also be made either by a human user or an automatic computer routine. Either a human user or a computer algorithm may inspect the angiography data and estimate which frame corresponds to the initial frame of the pullback. In the example shown in FIG. 3, the initial angiography frame is the second frame of the dataset. The radio-opaque marker M will not appear to move until the subsequent angio frame 3, since the initial OCT pullback frame 3 is generated with the catheter at an initial resting position. Knowing the time stamps associated with OCT frame 3 and angiography frame 2, the time period T3 can be calculated and applied to realign the two datasets. FIG. 4 includes an overview of these method steps and other related or supplemental steps as shown. Exemplary steps 10 to 80 are shown. Steps can be omitted as optional, performed simultaneously, or performed out of order in one or more embodiments.

In one embodiment, the disclosure relates to the implementation of various steps or a subset thereof. The steps include acquiring OCT data during OCT probe pullback; acquiring angiography data during OCT probe pullback; determining initial frame of OCT probe pullback from set of OCT frames; determining initial angiography frame that corresponds to initial frame of OCT probe pullback; determining time delay between initial OCT frame and initial angiography frame; selecting minimum time delay from multiple calibration trials; aligning OCT and angiography frames using minimum time delay; and displaying one or more aligned OCT and angiography frames.

Figure 5A:
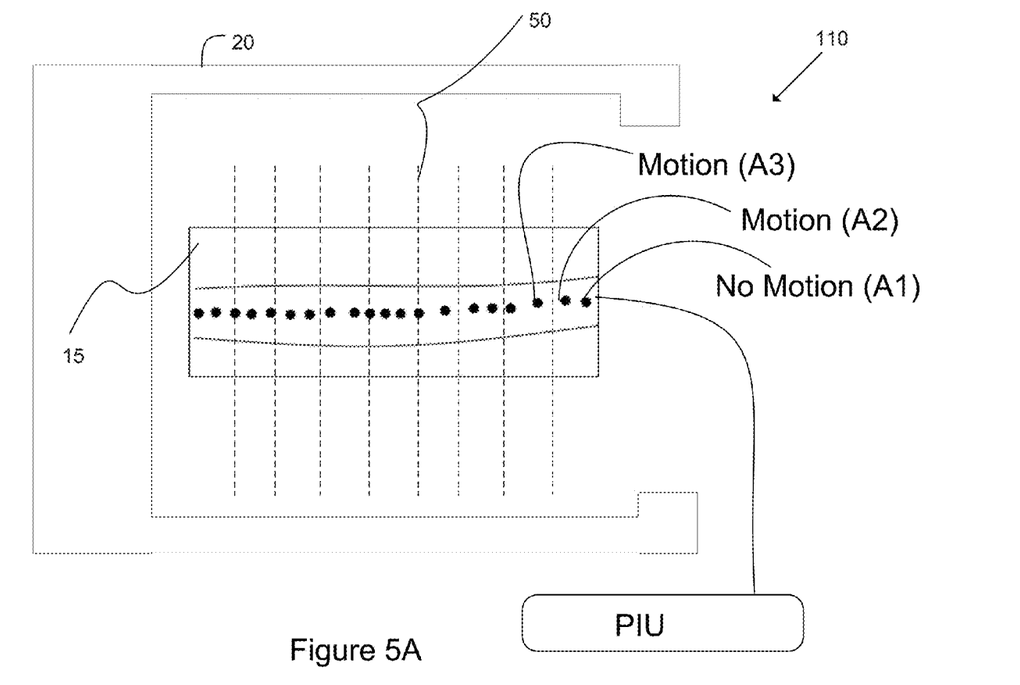
FIG. 5A is a schematic diagram of a data collection system that collects intravascular data and extravascular data during overlapping periods of time suitable for calibration using one or more methods of the disclosure.
Figure 5B:
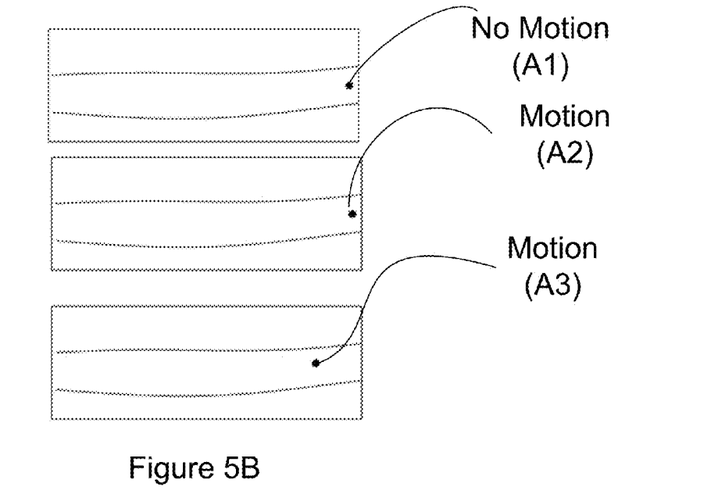
FIG. 5B is a schematic diagram that depicts three x-ray image frames of a blood vessel being imaged using the system of FIG. 5A that correspond to three points in time when a marker is not moving and then movement starts and then movement continues during an OCT pullback of a probe according to an embodiment of the disclosure.

FIG. 5A is a schematic diagram of an exemplary multi-modal system that include an angiography system shown as non-invasive system 20 and an OCT system that includes a probe with a marker M that has been pulled back through the blood vessel 15 shown. FIG. 5B shows the angiography frames corresponding to the pullback performed using the system of FIG. 5A. At a time prior to the initiation of the pullback A1, there is no marker motion. As shown, movement of the marker M occurs from rest moving from top to bottom from times A1 to A3 in the three angiography frames shown. Angiography frame motion is detected using machine vision, human inspection, or another mechanism.

In one embodiment, the angiography frame that is selected as the frame corresponding to initial probe or marker M movement is the frame before the frame for which motion is detected. Thus, even if there is movement at time A2, if the first frame that is detected as having movement is at time A3, A3 is not selected as the frame having initial movement. Instead, the frame before it, the middle frame corresponding to time A2 is selected. If frame A2 were detected as the frame having initial marker or probe motion then as part of the calibration method the first frame A1 would be set as the initial movement angiography frame. This approach effectively sets the origin at which motion starts earlier to help improve calibration results.

In general, in one embodiment frames of angiography data are processed, scanned or viewed to identify the occurrence of marker M movement or another probe feature. Once a frame has been identified as depicting probe movement, the frame immediately prior to that is identified for the purposes of the calibration method and the determination of time T3 as the angiography frame having initial movement. This process of adjusting for movement errors has been found to improve system calibration by reducing the likelihood that the frame of initial movement is missed.

Figure 6:
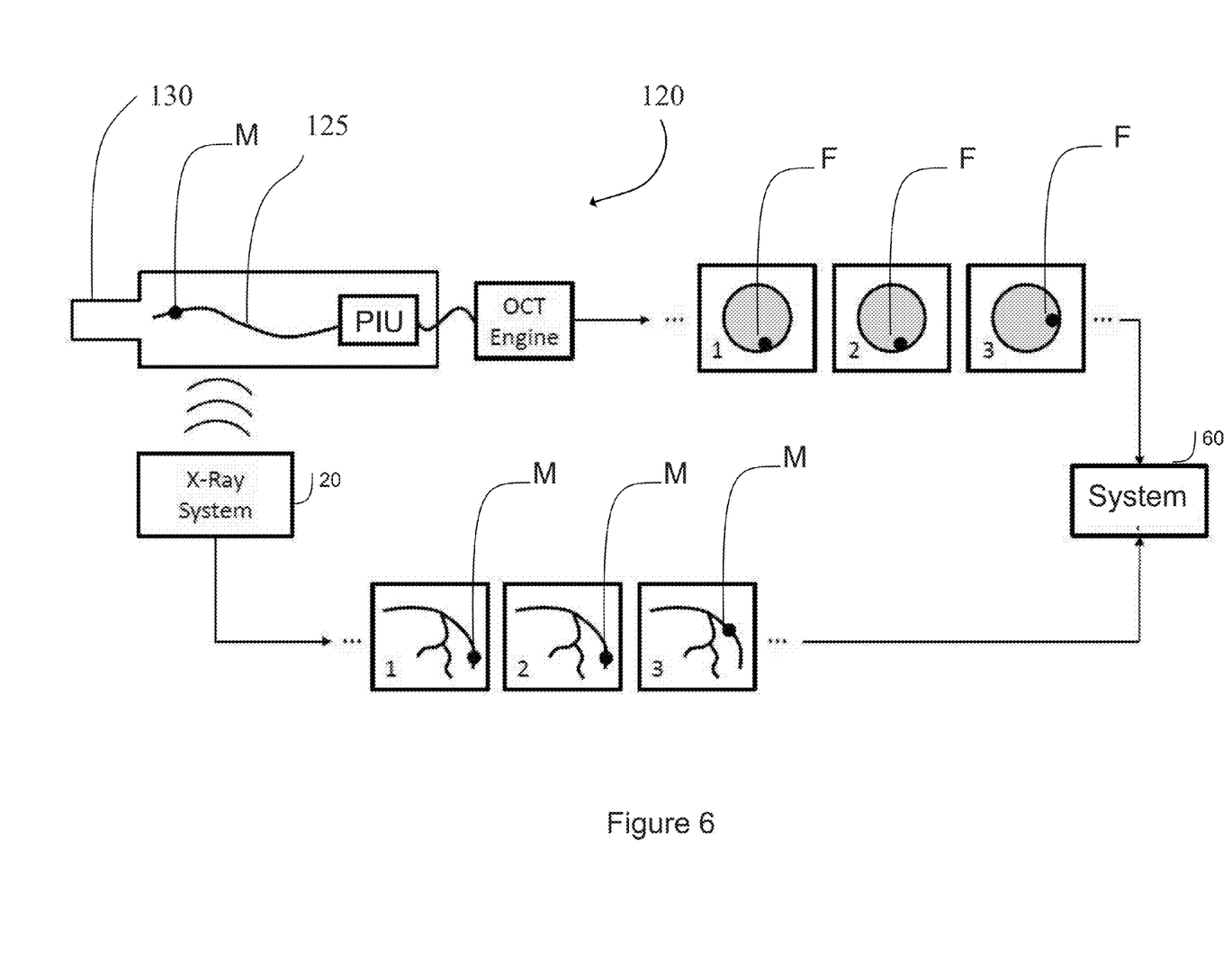
FIG. 6 illustrates an apparatus for performing temporal calibration according to an embodiment of the disclosure.

FIG. 6 illustrates a system 120 for conducting the temporal calibration methods described herein. The systems of FIGS. 1 and 5A and as otherwise described herein can also be used. An imaging catheter 125 is placed on a support 130 within the field of view of the X-ray system 20 such as an angiography system. In one embodiment, the imaging catheter includes an intravascular imaging probe such as an OCT probe. The OCT probe can be pulled back within a bore defined by the catheter. In one embodiment, the X-ray system 20 is activated first and acquires a cine sequence. If the OCT catheter includes a radio-opaque feature, such as a marker M, that moves in tandem with the catheter pullback, this motion will subsequently be visible on the acquired cine sequence.

In one embodiment, a marker M disposed on the probe such as near the lens of the OCT probe translates within the bore of a catheter along the support 130 as one or more motors in the PIU pull a torque wire in which is disposed an optical fiber in optical communication with a lens or beam director. Each frame of the angiography dataset is transmitted to an OCT computer, digitized by a frame grabber, and time stamped as the frame is stored in memory.

At the same time, an OCT dataset is generated by an OCT engine and transmitted to the same OCT computing device. Each OCT frame is time stamped as it enters memory. In this way the methods described herein such as shown in FIG. 2 can be executed and T3 can be calculated. The process of pulling an imaging probe back along a support while being imaged by an x-ray system can be performed a plurality of times to determine a set of candidate T3 values for the intravascular and X-ray based systems. As described herein, selecting the appropriate T3 value improves co-registration of frames generated by an intravascular system such as OCT and a non-invasive system such as angiography.

Based upon experimentation and testing to address errors detected during co-registration trials, it has been determined advantageous to conduct the temporal calibration procedure described above multiple times. By performing the calibration method multiple times it is possible to determine a more accurate assessment of T3. Performing multiple iterations of the calibration method to generate a set of T3 values addresses two sources of error. The first of these sources of T3 errors or variation is that OCT and angiography datasets are generated asynchronously (i.e., the OCT and angiography systems are independent devices with no master clocking mechanism). The second source of T3 errors or variation is that because the angiography frame rate is typically much lower than the OCT frame rate, the calculated value of T3 may vary by up to +/− one angiography frame period.

As a result of the lack of a master clocking system and the potential misalignment of frames due to frame rate differences, performing the calibration procedure multiple times and selecting the minimum value of T3 as a calibration parameter is performed. This optimization of the T3 calibration delay period by repeated calculation and minimum value selection allows for an accurate assessment of the actual lag time period T3 between the OCT and angiography datasets. Once a suitable T3 value has been determined, the OCT and angiography frames can be aligned on the same temporal reference frame. Each T3 in an exemplary set of T3 values can range from about 1 millisecond to about 500 milliseconds.

The smallest value in the set of N time delays is selected. The smallest value has been determined to be a suitable estimate from N samples. In one embodiment, N ranges from 2 to 15. In one embodiment, N ranges from 4 to 10. When a minimum T3 value from a set of N values is obtained, it can be used to identify an angiography frame, such as frame 2 in FIG. 3 which will have a relatively small amount of motion when compared for example to frame 3. The greater time lag associated with frame 3 results in the occurrence of a spatial positional error. This error can be understood in terms of an angiography frame being shown as co-registered with a particular OCT or other intravascular imaging frame while the distance between wherein the respective frames are incorrectly aligned and as much as between greater than 0 mm to about 3 mm apart in terms of their actual respective location in a subject.

Non-limiting Software Features and Embodiments for Implementing Angiography and Intravascular Data Calibration The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "calculating" or "comparing" or "aligning" or "synchronizing" or "operating" or "generating" or "co-registering" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure, in some embodiments, also relates to the apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present disclosure, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image procession using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing and processing instructions, or various types of data such as angiography data, OCT data, timestamps, calibration periods, marker position data, movement data, pixel information, calibration trial data and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

The use of arrow heads showing directionality in a given figure or the lack thereof are not intended to limit or require a direction in which information can flow. For a given connector, such as the arrows and lines shown connecting the elements shown in the figures information can flow in one or more directions or in only one direction as suitable for a given embodiment. The connections can include various suitable data transmitting connections such as optical, wire, power, wireless, or electrical connections.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It should be appreciated that various aspects of the claimed disclosure are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the disclosure claimed. Accordingly, what is desired to be secured by Letters Patent is the disclosure as defined and differentiated in the following claims, including all equivalents.

What is claimed is:

1. A calibration system comprising:
    an optical coherence tomography (OCT) probe comprising a marker, wherein the probe is configured to collect OCT data, wherein the probe is disposed within an imaging zone of an angiography system;
    an optical coherence tomography data processing system comprising
    a computing device comprising a processor, the computing device programmed to generate frames of OCT images based upon received intravascular probe signals and to receive angiography data comprising angiography frames, the processor configured to cause the computing device to determine a minimum time delay between an initial OCT frame and an initial angiography frame from a set of time delays; and
    one or more memory devices in electrical communication with the computing device; and
    a controller programmed to initiate a plurality of pullbacks of the OCT probe, in response to a control signal, during which OCT data is collected, and transmit each pullback initiation time to the one or more memory devices.

2. The system of claim 1 wherein the computing device comprises a calibration method stored in the one or more memory devices as instructions to cause the computing device to determine an initial frame of the OCT probe for each pullback.

3. The system of claim 1 wherein the computing device comprises a calibration method stored in the one or more memory devices as instructions to cause the computing device to determine an initial angiography frame that corresponds to an initial frame of OCT probe pullback.

4. The system of claim 1 wherein the computing device comprises a calibration method stored in the one or more memory devices as instructions to cause the computing device to determine a time delay between an initial OCT frame and an initial angiography frame.

5. The system of claim 4 wherein the calibration method further comprises instructions to cause the computing device to align OCT frames and angiography frames using the time delay.

6. The system of claim 1 further comprising a display in electrical communication with the optical coherence data processing system, wherein the computing device is programmed to align one or more OCT frames and one or more angiography frames using the minimum time delay and display one or more of such aligned frames.

7. The system of claim 1 wherein a frame rate of the optical coherence tomography data processing system is greater than a frame rate of the angiography system.

8. The system of claim 1 wherein the computing device is programmed to track pixel changes in angiography frames to identify marker movement.

9. The system of claim 8 wherein the computing device is programmed to use to marker movement to determine an initial angiography frame.

10. The system of claim 8 wherein the computing device is programmed to align an OCT frame with an angiography frame in response to tracked marker positions.

11. The system of claim 1 wherein the computing device is programmed to store a time an OCT pullback is initiated in the one or more memory devices.

12. The system of claim 1 wherein the computing device is programmed to determine a time delay between an angiography frame and an OCT frame.

\* \* \* \* \*